(12) United States Patent
Brummitt

(10) Patent No.: US 8,528,793 B2
(45) Date of Patent: Sep. 10, 2013

(54) ACTUATOR

(75) Inventor: Richard Brummitt, Hampshire (GB)

(73) Assignee: P. C. Cox Limited, Newbury Berkshire (GB)

( * ) Notice: Subject to any disclaimer, the term of this patent is extended or adjusted under 35 U.S.C. 154(b) by 276 days.

(21) Appl. No.: 12/978,695

(22) Filed: Dec. 27, 2010

(65) Prior Publication Data

US 2012/0160877 A1 Jun. 28, 2012

(30) Foreign Application Priority Data

Dec. 23, 2010 (EP) .................................... 10196813

(51) Int. Cl.
*B67D 7/60* (2010.01)

(52) U.S. Cl.
USPC .............................. 222/391; 222/326; 433/89

(58) Field of Classification Search
USPC .................. 222/391, 326, 327, 137; 42/1.14, 42/70.01, 10, 44, 64; 74/141.5, 557, 553, 74/523–528, 543–548; 433/90, 89, 80
See application file for complete search history.

(56) References Cited

U.S. PATENT DOCUMENTS

| | | | |
|---|---|---|---|
| 2,388,662 A | 11/1945 | Anderson et al. | |
| 2,582,156 A | 1/1952 | Peterson | |
| 2,692,706 A | 10/1954 | Wiksten | |
| 2,705,463 A | 4/1955 | Moore | |
| 2,839,945 A * | 6/1958 | Zion | 74/473.33 |
| 2,840,276 A | 6/1958 | Dreyer, Jr. et al. | |
| 3,254,806 A | 6/1966 | Madsen | |
| 3,353,537 A | 11/1967 | Knox et al. | |
| 3,431,953 A | 3/1969 | Rutherford | |
| 3,559,687 A | 2/1971 | Aslan | |
| 3,740,612 A | 6/1973 | Gauthier et al. | |
| 3,768,472 A | 10/1973 | Hodosh et al. | |
| 3,780,384 A | 12/1973 | Rivelle | |
| 3,819,115 A | 6/1974 | Soderman | |
| 3,980,209 A | 9/1976 | Collar | |
| 4,029,236 A | 6/1977 | Carson, Jr. et al. | |
| 4,116,364 A | 9/1978 | Culbertson et al. | |

(Continued)

FOREIGN PATENT DOCUMENTS

| | | |
|---|---|---|
| CH | 329614 | 4/1958 |
| DE | 1784336 | 8/1971 |

(Continued)

OTHER PUBLICATIONS

Web page printout, "Universal Coaxial Adhesive Dispenser", printed Jun. 24, 2009 http://www.5mix.com/Universal%20Dispenser.htm.

(Continued)

*Primary Examiner* — Kevin P Shaver
*Assistant Examiner* — Bob Zadeh
(74) *Attorney, Agent, or Firm* — Patterson Thuente Pedersen, P.A.

(57) ABSTRACT

An actuator for advancing a rod which enables release of the rod from an actuating mechanism by rotating the rod to allow the rod to be retreated. The actuator may also provide a mechanism for disabling the driving mechanism as the rod is fully advanced to prevent damage by excessive forces being applied to the rod. The actuating mechanism can be fully enclosed in a stock of a dispenser gun or applicator, facilitating cleaning of the dispenser gun. The disclosed dispenser gun is particularly suitable for dentistry applications.

15 Claims, 5 Drawing Sheets

(56) References Cited

U.S. PATENT DOCUMENTS

| | | | |
|---|---|---|---|
| 4,171,072 A * | 10/1979 | Davis, Jr. | 222/326 |
| 4,174,068 A | 11/1979 | Rudolph | |
| 4,264,021 A * | 4/1981 | Davis, Jr. | 222/326 |
| 4,273,269 A * | 6/1981 | Davis, Jr. | 222/326 |
| 4,290,091 A | 9/1981 | Malcolm | |
| 4,322,022 A * | 3/1982 | Bergman | 222/327 |
| 4,366,919 A | 1/1983 | Anderson | |
| 4,376,498 A | 3/1983 | Davis, Jr. | |
| 4,472,141 A | 9/1984 | Dragan | |
| 4,757,628 A * | 7/1988 | Bulfer | 42/1.14 |
| 5,125,836 A * | 6/1992 | Dragan et al. | 433/90 |
| 5,127,552 A | 7/1992 | Bauman et al. | |
| D329,277 S | 9/1992 | Keske et al. | |
| 5,163,584 A | 11/1992 | Huber et al. | |
| 5,277,099 A | 1/1994 | Powers | |
| 5,301,842 A | 4/1994 | Ritter | |
| 5,370,282 A | 12/1994 | Sedlmeier | |
| 5,489,207 A * | 2/1996 | Dragan et al. | 433/90 |
| 5,558,277 A | 9/1996 | Owen et al. | |
| D394,994 S | 6/1998 | Dreve | |
| 5,860,739 A | 1/1999 | Cannon | |
| D411,421 S | 6/1999 | Mayeur | |
| 6,116,902 A | 9/2000 | Schoedel et al. | |
| 6,135,328 A | 10/2000 | Schneider et al. | |
| 6,401,988 B1 | 6/2002 | Parent et al. | |
| 6,412,667 B1 * | 7/2002 | Huang | 222/327 |
| 6,454,138 B1 | 9/2002 | Greenhill et al. | |
| D479,305 S | 9/2003 | Zittel et al. | |
| 6,681,957 B1 | 1/2004 | Green | |
| 6,929,157 B2 * | 8/2005 | Orecchia et al. | 222/326 |
| 7,334,709 B1 | 2/2008 | Huang | |
| D583,639 S | 12/2008 | Axinte et al. | |
| D588,231 S | 3/2009 | Pellin et al. | |
| 7,632,251 B2 * | 12/2009 | Lin et al. | 604/187 |
| D608,858 S | 1/2010 | Baltz et al. | |
| D649,221 S | 11/2011 | Sinders et al. | |
| D660,105 S | 5/2012 | Brummitt | |
| D660,663 S | 5/2012 | Brummitt | |
| 2002/0092871 A1 | 7/2002 | Rickard et al. | |
| 2004/0126733 A1 * | 7/2004 | Ronvig | 433/90 |
| 2004/0216591 A1 | 11/2004 | Assadi et al. | |
| 2007/0102457 A1 * | 5/2007 | Campbell et al. | 222/333 |
| 2008/0149216 A1 | 6/2008 | Speck | |
| 2011/0095054 A1 | 4/2011 | Hughes | |

FOREIGN PATENT DOCUMENTS

| | | |
|---|---|---|
| DE | 3031939 | 8/1980 |
| DE | 3420324 | 12/1985 |
| DE | 9000957 | 4/1990 |
| DE | 9011965 | 10/1990 |
| DE | 102005038621 | 3/2007 |
| EP | 0276665 | 8/1988 |
| EP | 0406113 | 1/1991 |
| EP | 0443611 | 3/1991 |
| EP | 0436155 | 7/1991 |
| EP | 0448375 | 9/1991 |
| EP | 0525562 | 2/1993 |
| EP | 0551998 | 7/1993 |
| FR | 984352 | 7/1951 |
| GB | 793277 | 4/1958 |
| GB | 1555455 | 11/1979 |
| GB | 1589381 | 5/1981 |
| GB | 2276365 | 9/1994 |
| NL | 6602366 | 8/1966 |
| WO | WO2005/095225 | 10/2005 |
| WO | WO2006/106215 | 10/2006 |
| WO | WO2011/052891 | 5/2011 |

OTHER PUBLICATIONS

Cox Sealant Applicators, Jun. 17, 2008. http://www.toolbarn.com/product/CCM-380-10/.

GB Search Report from GB Application No. GB0918585.1 dated May 11, 2010.

European Search Report for European Application No. 10196812.1 dated Mar. 9, 2012.

European Search Report for European Application No. EP91102643 dated Oct. 3, 1991.

European Search Report for European Application No. EP90401861 dated Mar. 13, 1991.

European Extended Search Report for European Application No. 10196812.1 dated Jul. 11, 2011.

European Extended Search Report of European Application No. 10196810.5 dated Jul. 19, 2011.

European Extended Search Report of European Application No. 10196813.9 dated Jun. 28, 2011.

European Extended Search Report of European Application No. 10196816.2 dated Jun. 22, 2011.

International Search Report of International Application No. PCT/FR2006/000710 dated Jul. 13, 2006.

Application and File History for U.S. Appl. No. 13/336,462, filed Dec. 23, 2011, inventor Brummitt.

Application and File History for U.S. Appl. No. 13/336,480, filed Dec. 23, 2011, inventor Brummitt.

Application and File History for U.S. Appl. No. 13/336,517, filed Dec. 23, 2011, inventor Brummitt.

Application and File History for U.S. Appl. No. 12/910,462, filed Oct. 22, 2010, inventor Hughes.

Web page printout, "Complet Applicator Super Strong Single-dose applicator", Dec. 20, 2010. http://www.sdi.com.au/en.complet-applicator/.

Web page printout, "Complet Applicator (SDI) Interguide Dental and Medical Supply", Dec. 20, 2010. http://interguidedental.com/Complet-Applicator-SDI-p13579.html.

* cited by examiner

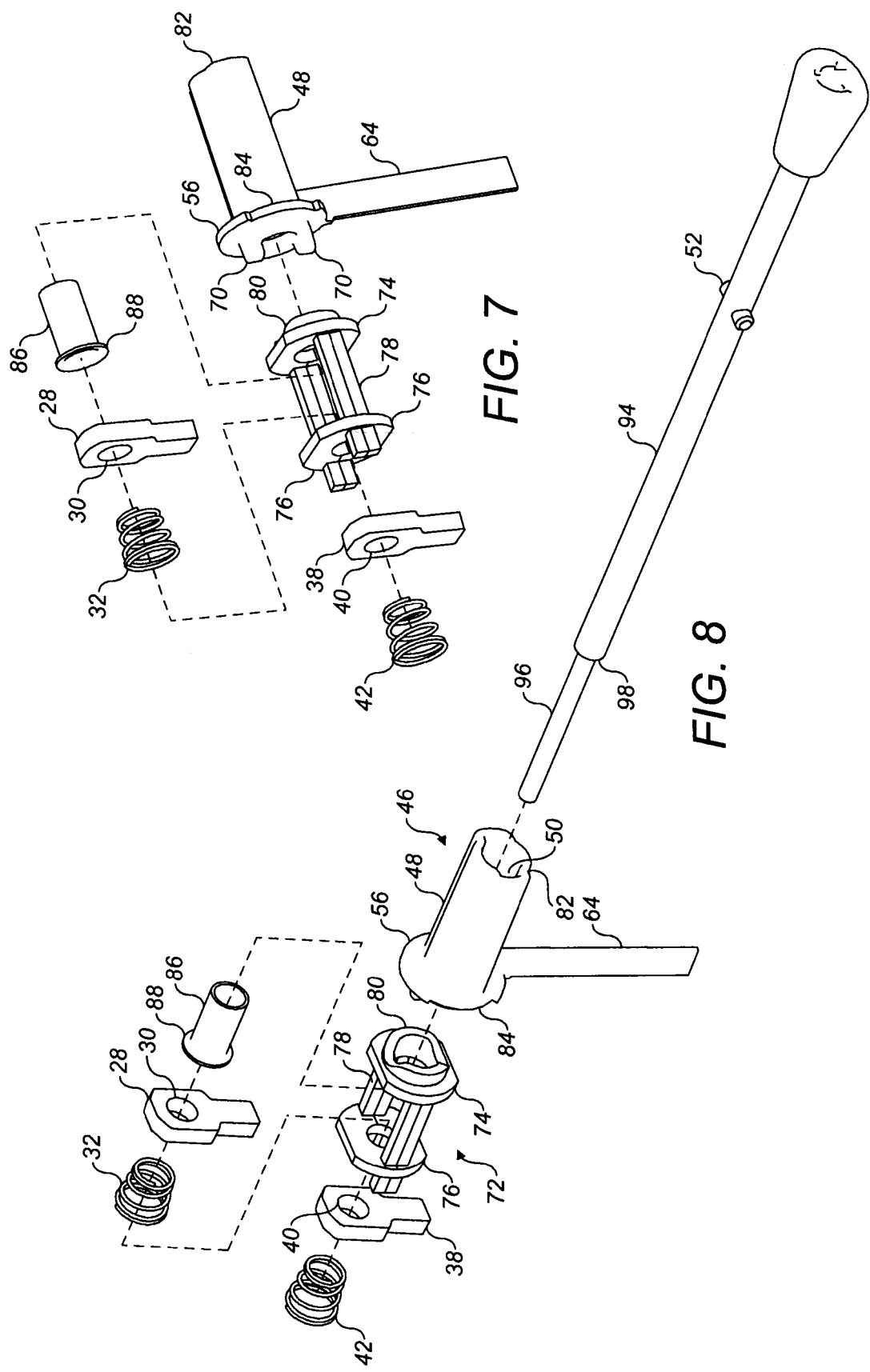

ACTUATOR

RELATED APPLICATION

The present application claims priority to EP Application No. 10196813.9 filed Dec. 23, 2010, which is incorporated herein in its entirety by reference.

TECHNICAL FIELD

The present invention relates to an actuator for advancing a rod and, in particular, a dispenser or applicator using such an actuator to apply a dispensing pressure to a viscous material. More particularly, the present invention relates to such a dispenser or applicator for dentistry applications.

BACKGROUND ART

Viscous material, such as mastic caulking material, is commonly supplied in a cartridge having a discharge nozzle. The cartridge can be mounted in a dispensing appliance, often called a dispensing gun or applicator. An example of such a dispensing gun is described in British patent GB1555455. The gun has a plunger or a push rod slideably mounted in a cartridge. The cartridge is mounted in a keep before the plunger. The plunger is advanced by means of a catch plate linked to a trigger lever engaging the rod. When a dispensing force is applied to the trigger lever, the plunger forces a piston, inside one end of the cartridge, forward to urge the material from the nozzle at the other end. The trigger and catch plate are reset at the end of a dispensing stroke and the dispensing force can be reapplied.

Between trigger strokes the plunger is held against the piston by means of a locking plate. In order to retreat the plunger, for example to remove the cartridge, a force is applied to the locking plate to disengage the locking plate from the rod and allow retreat of the rod. The locking plate can be arranged to either substantially prevent any retreat of the rod during dispensing or to allow a small amount of retreat of the rod to release pressure applied to the cartridge, as disclosed, for example, in European patent EP0448375. In order to be able to retreat the plunger, the locking plate must be accessible so that a releasing force can be applied to it, either directly or by an intermediate mechanical linkage where the locking plate is within a housing together with the remaining actuating mechanism, for example as disclosed in U.S. Pat. No. 5,370,282.

The inventors have realized that, for a number of reasons, it may be undesirable to require access to the locking plate or a corresponding release lever or button in order to release the locking plate to allow retreat of the rod. For example, if the locking plate or lever is arranged such that it can be actuated by the thumb of a user's hand holding the gun to leave the other hand free to retreat the rod, this will compromise the design freedom in designing the gun, in particular for dispensing guns of overall small size. Similarly, the need for an external locking plate or lever tends to make the dispensing gun more difficult to clean, even if the remaining actuating mechanism is enclosed in a housing. These considerations are particularly relevant for dentistry applications, where the nature of the work and the small quantities of material to be dispensed means that the dispenser is likely to be of a small form factor and where the ease of maintaining the dispensing gun cleanliness is paramount. However, it will be understood that these considerations are not limited to dentistry applications.

SUMMARY OF THE INVENTION

In an embodiment of the invention, there is provided an actuator for advancing a rod, the actuator comprising a catch member for engaging the rod, a trigger member for moving the catch member to advance the rod in one direction and a locking member for engaging the rod to prevent the rod retreating in the other direction. The actuator further comprises a release arrangement for transforming a torque applied to the rod into a releasing force disengaging the locking member to enable retreat of the rod in the other direction.

The release arrangement enables the release of the locking member by rotation of the rod, thereby dispensing with the need for a locking plate (or corresponding lever) which is separately actuatable by user. Rotation of the rod thus urges the locking member away from a configuration in which it is engaged with (bites on) the rod, preventing the rod's retreat, to disengage the locking member from the rod. The user can release and retreat the rod with a single hand gesture, thereby addressing the problems discussed above and increasing ease of use of the actuator generally.

In some embodiments, the release arrangement comprises a cam member and a cam follower. The cam member slidingly accepts the rod and defines a cam at one end. The cam engages the cam follower to transfer rotation of the rod to translation of the cam follower, thereby applying the releasing force to the locking member. In embodiments where the catch member is biased to engage the rod when the trigger member is not actuated, the release arrangement is arranged to transform the torque applied to the rod to a releasing force disengaging the catch member, as well as the locking member, to enable retreat of the rod. In some embodiments, the locking member and/or catch member are biased into an engaged attitude with respect to the rod and the releasing force causes rotation of the locking and/or catch member away from the engaged attitude.

In some embodiments, the locking member is forward of the catch member in the one direction. This enables a space efficient arrangement of the actuator in a confined housing, making use of the space forward of the catch member to accommodate the locking member.

In some embodiments, the actuator provides end of stroke release, releasing the catch member when the rod reaches a predetermined (usually fully advanced) position to prevent further pressure being applied to the rod and the corresponding risk of damaging the actuator and/or dispenser or dispensing cartridge to which the actuator is applied. In these embodiments, the actuator comprises a holding member for holding the catch member in a disengaged relationship with respect to the rod when the rod is advanced to the predetermined position. At this point, further actuation of the trigger member does not advance the rod any further. In some embodiments, the rod comprises a protrusion, for example a pin extending on one or both sides of the rod, for engaging the holding member and thus to advance the holding member with the rod as the rod advances to a predetermined position. In some embodiments, the cam member defines a channel in which this protrusion is slideably accepted to cause the cam member to rotate with the rod. In some embodiments, the holding member is a sleeve disposed between the rod and the cam member, resulting in a compact arrangement in which the rod is supported by the sleeve and cam member to provide a journal close to the actuating mechanism and, in particular, the catch member.

Irrespective of the presence of a holding member, in some embodiments the rod includes a protrusion, for example as described above, and the cam member defines a channel slideably accepting this protrusion to cause the cam member to rotate with the rod.

In an embodiment of the invention, there is provided a dispenser for dispensing a viscous material, the dispenser comprising an actuator as described above for applying a dispensing pressure to the viscous material.

In some embodiments, the dispenser fully encloses the catch member, locking member and release arrangement. The dispenser is, in some embodiments, arranged for use in dentistry.

In some embodiments of the invention, there is provided a dispenser for dispensing a viscous material, the dispenser comprising an actuator for advancing a rod to apply a dispensing pressure to the viscous material. The dispenser comprises a window through which the advance of the rod can be observed. In some embodiments, the window comprises graduations indicating the amount of advance of the rod as a result of a complete actuation of the trigger member. In some embodiments, the feature is a shoulder between portions of the rod having different diameters.

In some embodiments of the invention, there is provided an actuator for advancing a rod, the actuator comprising means for advancing the rod in response to actuation of a trigger lever and means for preventing retreat of the rod. The actuator further comprises means for releasing the rod in response to rotation of the rod in order to enable retreat of the rod.

An embodiment of the invention is now described by way of example only and with reference to the accompanying drawings.

BRIEF DESCRIPTION OF THE DRAWINGS

FIG. 7 is an exploded view of components of an actuating mechanism for advancing a rod of the dispenser; and FIG. 8 is another exploded view of components of the actuating mechanism, including the rod.

DETAILED DESCRIPTION

Figure 1:
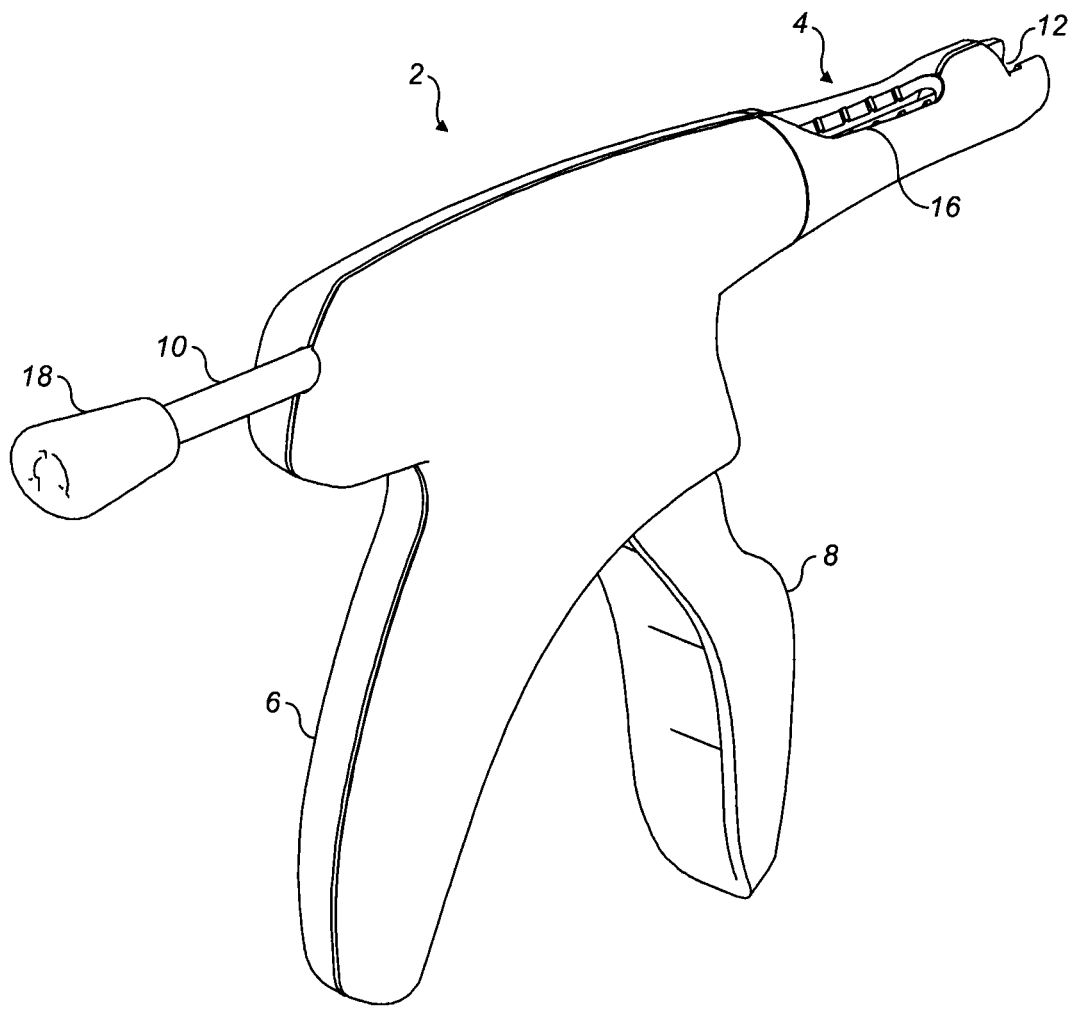
FIG. 1 is a perspective view of a dispenser in accordance with an embodiment of the invention.
Figure 2:
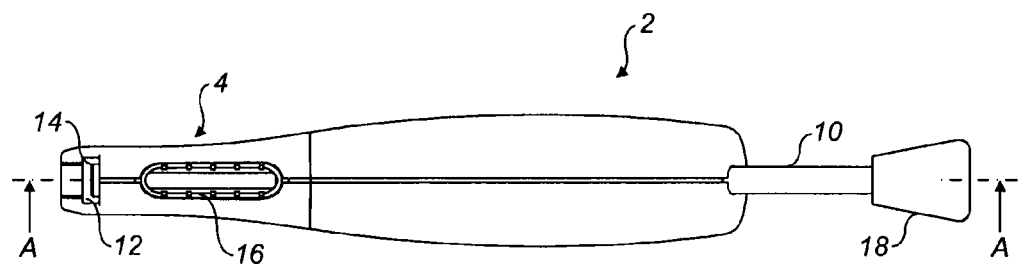
FIG. 2 is a top elevation view of the dispenser.
Figure 3:
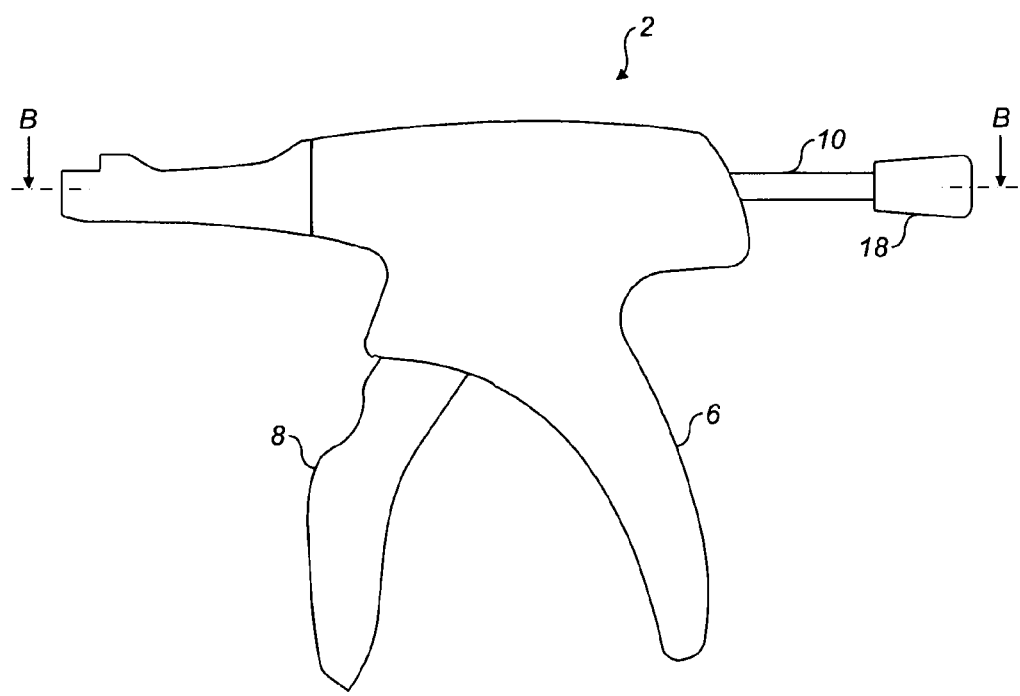
FIG. 3 is a side elevation view of the dispenser.
Figure 4:
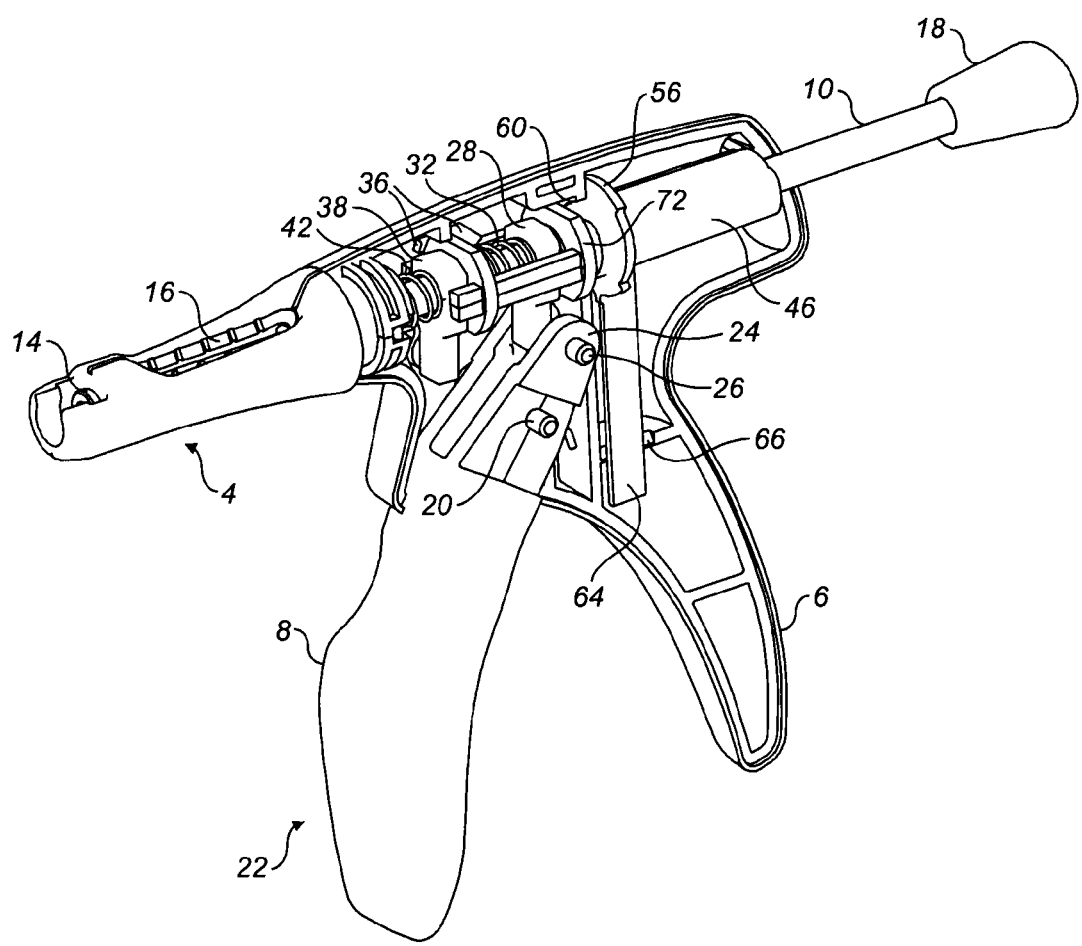
FIG. 4 is a view exposing an actuating mechanism inside the dispenser.
Figure 5:
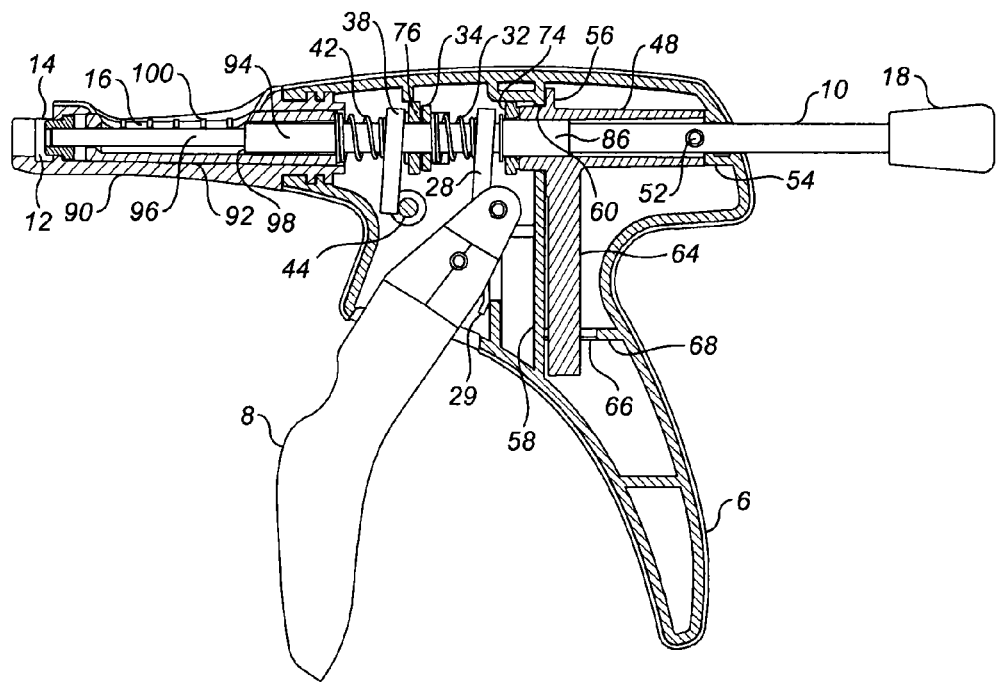
FIG. 5 depicts a partial cross-section along the line A-A of FIG. 2.
Figure 6:
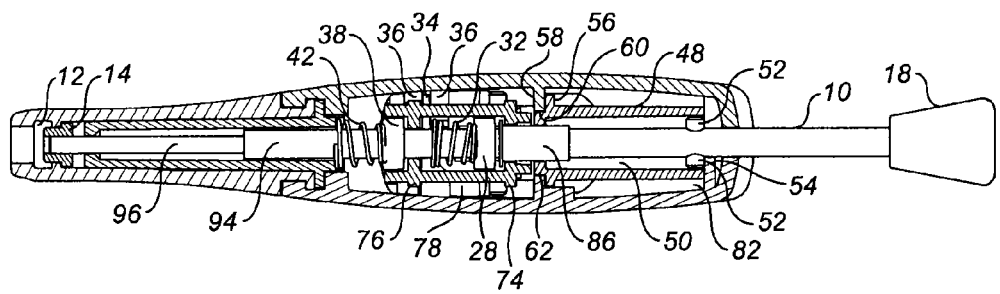
FIG. 6 depicts a partial cross-sectional view along the line B-B in FIG. 3.

With reference to FIGS. 1, 2 and 3, a dispenser or applicator comprises an actuator 2 and a cartridge holder 4. The actuator 2 comprises a stock 6 and a trigger lever 8 movable relative to the stock 6. A rod 10 is disposed slideably within the stock 6 and a mechanism inside the stock 6, described in detail below, is arranged such that actuation of the trigger lever 8 causes the rod 10 to advance with respect to the stock 6 and the cartridge holder 4 into a cartridge (not shown) held in a slot 12 of the cartridge holder 4. A positioning member 14 is biased by a disc spring (non shown) to protrude into the slot 12, thereby applying a resilient positioning force to a rear end of the cartridge held in the slot 12. The cartridge holder 4 comprises a window 16 through which the advance of the rod 10 can be observed. At a rear end, the rod 10 carries a knob 18 for enabling a user of the dispenser to rotate the rod 10 in order to release the mechanism inside the stock 6 such that the rod 10 can be retreated, for example to change a cartridge once the rod 10 has been advanced into it.

With reference to FIGS. 4 to 8, a driving mechanism of the actuator 2 comprises the trigger lever 8 being pivotably secured to the stock 6 by pivot 20. A lower portion 22 of the trigger lever 8 is configured for actuation by a user's fingers pulling the trigger lever 8 towards the stock 6 and an upper portion 24 opposed to the lower portion 22 across the pivot 20 comprises a trigger pin 26 for engaging a catch plate 28. The trigger lever 8 is biased into a rest orientation with the lower portion 22 disposed away from the stock 6 by a torsion spring 29. The catch plate 28 has an aperture 30 accepting the rod 10 and is biased against the trigger pin 26 and into engagement with the rod 10 by a first helical spring 32 disposed forward of the catch plate 28 towards the cartridge holder 4 and resting against a forked cross member 34 providing a seat for the first helical spring 32. The forked cross-member 34 accepts the rod 10 between its prongs extending across the interior space inside the stock and locating between support struts 36 at their free ends. A locking plate 38 has an aperture 40 accepting the rod 10 and is disposed forward of the catch plate 28 and the forked cross member 34. A second helical spring 42 rests against a rear end of the cartridge holder 4 providing a seat for the second helical spring 42. The second helical spring 42 biases the locking plate 38 against a cross bar 44 rearwards of the locking plate 38 and thereby into engagement with the rod 10.

The arrangement of the catch plate 28 and locking plate 38 means that they bite on the rod when the rod is pulled rearwards relative to the catch and locking plates 28, 38 but allow the rod to be pushed forward. Consequently, the catch plate 28 bites on the rod 10 when the trigger lever 8 is pulled towards the stock 6, advancing the rod, and slides across the rod as the trigger lever 8 returns to its rest position away from the stock 6, while the rod 10 is held in position by the locking plate 38 biting on it. Thus, repeated actuation of the trigger lever 6 towards the stock 6 advances the rod 10 in a forward direction towards the slot 12 with each stroke of the trigger lever 8.

A cam member 46 comprises a sleeve 48 accepting the rod 10 and defines channels 50 accepting protruding portions of a pin 52 disposed in a hole through the rod 10. An interior forward wall of the channels 50 limits the advance of the pin 52 in the channels 50 and hence advance at the rod 10. Similarly, a stop 54 extending from an interior wall of the stock 6 limits the retreat of the rod 10 in the other direction. At one end facing the cartridge holder 4 the cam member 46 defines a flange 56 abutting an interior wall 58 of the stock 6. The interior wall 58 defines an aperture 60 rotatably accepting a front end 62 of the cam member 46. A leaf spring 64 extends from the cam member 46 in a direction perpendicular to the direction of the pin 52 between the channels 50, the cam member 46 and the leaf spring 64 being molded in one piece. The leaf spring 64 is held in an aperture 66 of a strut wall 68 of the stock 6 and defines a rest orientation for the cam member 46 in which the pin 52 and channels 50 extend substantially perpendicularly on either side of a mid plane of the stock 6. Cams 70 extend forward from the end 62 on either side of the rod 10, aligned with the direction of the leaf spring 64.

A cam follower 72 is disposed generally around the rod 10 forward of the cam member 46 and comprises a first portion 74 disposed between the cam member 46 and the catch plate 28 linked to a second portion 76 by a linking portion 78. The second portion is disposed between the forked cross member 34 and the locking plate 38. The linking portions 78 extend between the first and second portions 74, 76 on either side of the rod 10 and the catch plate 28 and first helical spring 32 around it and between the prongs of the forked cross member 34. Further, the linking portion 78 extends forward of the second portion 76 on either side of the locking plate 38. In this way, the cam follower 72 is held in rotational alignment with the catch plate 28 and locking plate 38, and hence, the stock 6, preventing rotation of the cam follower 72 relative to the stock while allowing reciprocating movement of the cam follower 72 along the rod 10. A cam engaging surface 80 of the first portion 74 face the cams 70 and is shaped to have troughs aligned with the cams 70 in the rest orientation of the cam member 46 and lobes to the sides of the troughs aligned perpendicularly to a direction defined by the cams 70 in the rest orientation. In this orientation, the cam member 46 and cam follower 72 are disposed relative to each other such that the cams 70 are disposed inside the troughs and between the lobes of the cam engaging surface 80.

The cam member 46 is constrained for only rotational movement relative to the stock 6 by virtue of being disposed in the aperture 60 with movement along the direction of the rod being prevented by the flange 56 engaging the wall 58 and a rear end 82 of the cam member 46 engaging the stop 54. Excessive rotation of the rod 10 and cam member 46 is prevented by a nub (not shown) protruding from an interior surface of the stock 6 locating inside a recessed portion 84 of the flange 56, thus limiting the rotational range to the angular extent of the recessed portion 84 of the flange 56.

As described above, both the catch plate 28 and locking plate 38 prevent retreat of the rod 10. By virtue of the cam member 46 and cam follower 72, a user can disengage the catch plate 28 and locking plate 38 by rotating the rod 10 by means of the knob 18. The rotation of the rod 10 is transferred to the cam member 46 by the pin 52. As the cam member 46 rotates, the cams 70 engage the lobes between the troughs of the cam engaging surface 80, urging the cam follower 72 away from the cam member 46, the interaction between the cams 70 and cam engaging surface 80 thus causes the cam follower 72 to move longitudinally forward along the rod 10 to engage the catch plate 28 and locking plate 38 with, respectively, the first portion 74 and second portion 76, causing the catch plate 28 and locking plate 38 to rotate away from their respective engaged attitudes with respect to the rod 10 in which they bite on the rod 10 until the catch plate 28 and locking plate 38 are held between the respective helical spring and portion of the cam follower 72 in a disengaged attitude relative to the rod 10 so that the rod can slide freely allowing the rod 10 to be retreated.

A bushing 86 is disposed around the rod 10 and the cam is slidingly accepted by member 46 and the first portion 74 of the cam follower 72. A lip 88 prevents the bushing 86 from sliding the rearwards past the first portion 74. The length of the bushing is selected such that the pin 52 engages a rear aspect of the bushing 86 as the rod 10 approaches the end of its forward travel and takes the bushing 86 with it on the last stroke of the trigger lever 6, holding the catch plate 28 in a disengaged attitude relative to the rod 10 between the first helical spring 32 and the lip 88 at or close to the position of the trigger pin 26 when the trigger lever 6 is fully depressed. As a result further actuation of the trigger lever 6 applies no further advancing force to the rod 10, the trigger pin 26 not making contact with the catch plate 28 over all or nearly all of the stroke of the trigger lever 6. The interaction between the pin 52 and the bushing 86 thus acts as a end of stroke release mechanism, ensuring that no, or no significant, advancing forces are applied to the rod 10, thus preventing potential damage to the mechanism at the end of the stroke.

The cartridge carrier 4 comprises an outer portion 90 and an insert 92, acting as a bushing for the rod 10. The rod 10 comprises a first portion 94 which is of a larger diameter than a second portion 96, defining a shoulder 98 between the two portions. The first portion 94 is engaged by the catch plate 28 and the locking plate 38 and the second portion 96 acts as a plunger advanceable into a cartridge held in the slot 12. The first portion 94 is journaled by the insert 92 adjacent to the locking plate 38 and by the bushing 86 adjacent to the catch plate 28. The window 16 described above extends through the outer portion 90 and insert 92 so that the rod 10 is visible. The window 16 has graduations 100 corresponding to the position of the shoulder 98 at the end of each stroke between the rod's 10 fully advanced and fully retreated positions. By virtue of the window 16 and graduations 100, a user can immediately see how many strokes of the trigger lever remain before the material in the cartridge is fully dispensed, at least for cartridges in which the range of movement of the cartridge's piston corresponds to the range of movement of the rod 10. In any event, the graduations 100 provide a measure of the amount of material remaining which can be dispensed with the dispenser.

Most components of the above described dispenser are molded from suitable plastic materials, for example glass filled Nylon, polycarbonate (PC), polyethersulfate (PES), ABS. In the embodiment depicted in the drawings there are nine separately molded components, the knob 18, the cartridge holder 16 outer portion 90 and insert 92, the positioning member 14 the cam follower 72, the cam member 46, the trigger lever 8 and two halves of the stock 6. The cartridge holder 4 is held relative to the slot by flanges engaging corresponding slots in the stock and the two halves of the stock are ultrasonically welded together although other securing methods, such as adhesive bonding, can equally be applied. The remaining components are made of suitable metal materials, for example stainless steel. In one particular embodiment specifically adapted for the use in dentistry, plastic materials that can be sterilized in an autoclave are employed, such as PES or PC and stainless steel is used for all non-plastic parts.

It will be understood that the above description of an embodiment of the invention has been made by way of example to illustrate aspects of the invention and that many alterations, modifications and juxtapositions of the features described above are possible and intended to be covered by the scope of the appendent claims.

For example, the catch plate may not be engaged with the rod 10 in the rest configuration of the trigger lever 6, with no dispensing force applied to the trigger lever 6, but rather rest in a disengaged attitude from the rod 10 against an abutment or other feature of the stock 6, so that the cam follower 72 only needs to release the locking plate 38 in order to enable retreat of the rod 10. It is generally possible to reverse the order of the catch plate 28 and locking plate 38 and in embodiments where the catch plate 28 is not engaged with the rod 10 in the trigger lever's 8 rest configuration, this enables the cam follower 72 to be simplified so that only a single portion carrying the cam engaging surface 80 and arranged to disengage the locking plate 38 is necessary. Likewise, the bushing 86 may be omitted from some embodiments, with a corresponding reduction in the aperture of the cam member 46 and/or cam follower 72 being possible to ensure secure journaling of the rod 10.

While a particular cam arrangement for transforming rotating of the rod into a releasing force for releasing the locking plate 32 and/or catch plate 28 has been discussed above, it will be appreciated that many other arrangements are possible in alternative embodiments of the invention. For example, the cam member may have only a single cam, omitting one of the cams of the specific embodiment described above. In yet other embodiments, a cam or cams are directly attached to an arm or arms extending away from the rod in a suitable orientation to directly interact with the catch and/or locking plate to nudge them into a disengaged position in response to rotation of the rod. Similarly, a cam or cams directly nudging the locking and/or catch plate can be mounted on a gear or cog wheel directly or indirectly driven by rotation of the rod. Numerous other arrangements are equally possible.

Finally, it will be understood that the skilled person would select suitable materials and/or form factors, as well as open or closed stock designs and cartridge holders with or without a window for observing the advance of the rod, as a function of the particular application, without departing from the invention.

The invention claimed is:

1. An actuator for advancing a rod, the actuator comprising:
a catch member for engaging the rod;
a trigger member for moving the catch member to advance the rod in one direction;
a locking member for engaging the rod to prevent the rod retreating in the other direction;
a release arrangement for transforming a torque applied to the rod to a releasing force disengaging the locking member to enable retreat of the rod in the other direction; and
a holding member for holding the catch member in a disengaged relationship with respect to the rod when the rod is advanced to a predetermined position, thereby preventing advance of the rod past the predetermined position in response to actuation of the trigger member.

2. An actuator as claimed in claim 1, in which the release arrangement comprises a cam member and a cam follower, the cam member slideably accepting the rod and defining a cam at one end, the cam engaging the cam follower to transform rotation of the rod to translation of the cam follower, thereby applying the releasing force to the locking member.

3. An actuator as claimed in claim 1, the locking member being biased into an engaged attitude with respect to the rod, the releasing force disengaging the locking member causing rotation of the locking member away from the engaged attitude.

4. An actuator as claimed in claim 1, in which the release arrangement is arranged to transform the torque applied to the rod to a releasing force disengaging the catch member to enable retreat of the rod.

5. An actuator as claimed in claim 4, the catch member being biased into an engaged attitude with respect to the rod, the releasing force disengaging the catch member causing rotation of the catch member away from the engaged attitude.

6. An actuator as claimed in claim 1, in which the locking member is forward of the catch member in the one direction.

7. An actuator as claimed in claim 1, in which the rod comprises a protrusion for engaging the holding member to advance the holding member with the rod as the rod advances to the predetermined position.

8. An actuator as claimed in claim 2, in which the rod comprises a protrusion slideably accepted in a channel defined by the cam member to cause the cam member to rotate with the rod.

9. A dispenser for dispensing a viscous material, the dispenser comprising an actuator as claimed in claim 1 for applying a dispensing pressure to the viscous material.

10. A dispenser as claimed in claim 9, the dispenser enclosing the catch member, locking member and release arrangement.

11. A dispenser as claimed in claim 9 comprising a window through which advance of the rod can be observed.

12. A dispenser as claimed in claim 9 for use in dentistry.

13. An actuator for advancing a rod, the actuator comprising:
a catch member for engaging the rod;
a trigger member for moving the catch member to advance the rod in one direction;
a locking member for engaging the rod to prevent the rod retreating in the other direction;
a release arrangement for transforming a torque applied to the rod to a releasing force disengaging the locking member to enable retreat of the rod in the other direction, the release arrangement comprising a cam member and a cam follower, the cam member slideably accepting the rod and defining a cam at one end, the cam engaging the cam follower to transform rotation of the rod to translation of the cam follower, thereby applying the releasing force to the locking member; and
a holding member for holding the catch member in a disengaged relationship with respect to the rod when the rod is advanced to a predetermined position, thereby preventing advance of the rod past the predetermined position in response to actuation of the trigger member, the rod comprising a protrusion for engaging the holding member to advance the holding member with the rod as the rod advances to the predetermined position, the cam member defining a channel in which the protrusion is slideably accepted to cause the cam member to rotate with the rod.

14. An actuator as claimed in claim 13, the holding member being a sleeve disposed between the rod and the cam member.

15. An actuator for advancing a rod, the actuator comprising:
a catch member for engaging the rod;
a trigger member for moving the catch member to advance the rod in one direction;
a locking member for engaging the rod to prevent the rod retreating in the other direction; and
a release arrangement for transforming a torque applied to the rod to a releasing force disengaging the locking member to enable retreat of the rod in the other direction, the release arrangement including a cam member and a cam follower, the cam member slideably accepting the rod and defining a cam at one end, the cam engaging the cam follower to transform rotation of the rod to translation of the cam follower, thereby applying the releasing force to the locking member,
wherein the rod includes a protrusion slideably accepted in a channel defined by the cam member to cause the cam member to rotate with the rod.

* * * * *